(12) United States Patent
Mosse et al.

(10) Patent No.: US 6,709,388 B1
(45) Date of Patent: Mar. 23, 2004

(54) PASSAGE-TRAVELLING DEVICE

(75) Inventors: Charles Alexander Mosse, London (GB); Timothy Mills, London (GB); Paul Swain, London (GB)

(73) Assignee: University College London Hospitals NHS Trust, London (GB)

( * ) Notice: Subject to any disclaimer, the term of this patent is extended or adjusted under 35 U.S.C. 154(b) by 0 days.

(21) Appl. No.: 10/048,560

(22) PCT Filed: Aug. 3, 2000

(86) PCT No.: PCT/GB00/03023

§ 371 (c)(1),
(2), (4) Date: May 9, 2002

(87) PCT Pub. No.: WO01/08548

PCT Pub. Date: Feb. 8, 2001

(30) Foreign Application Priority Data

Aug. 3, 1999 (GB) ............................................. 9918184

(51) Int. Cl.[7] .................................................. A61B 1/04
(52) U.S. Cl. .......................... 600/114; 600/302; 607/40; 607/133
(58) Field of Search ................................. 600/114, 109, 600/112, 160, 302; 607/40, 133, 138, 36

(56) References Cited

U.S. PATENT DOCUMENTS

| | | |
|---|---|---|
| 3,411,507 A | 11/1968 | Wingrove |
| 4,176,662 A | 12/1979 | Frazer |
| 6,240,312 B1 * | 5/2001 | Alfano et al. ................ 600/476 |
| 6,324,418 B1 * | 11/2001 | Crowley et al. ............ 600/476 |
| 6,453,199 B1 * | 9/2002 | Kobozev ..................... 607/40 |

FOREIGN PATENT DOCUMENTS

| | | | |
|---|---|---|---|
| FR | 2237648 | 2/1975 | |
| WO | WO 96/00517 A1 | 1/1996 | |
| WO | WO 97/36646 | * 10/1997 | ............ A61N/1/36 |
| WO | WO 98/11816 A1 | 3/1998 | |
| WO | WO 99/34726 A1 | 7/1999 | |

OTHER PUBLICATIONS

English translation of the Zacouto reference (FR 2,237,648).*

* cited by examiner

*Primary Examiner*—John Mulcahy
(74) *Attorney, Agent, or Firm*—Fleshner & Kim, LLP

(57) ABSTRACT

A self-propelling device (1) is adapted to travel through a passage (3) having walls containing contractile tissue, the device (1) comprising a body (2) and at least one contractile tissue-stimulating means for stimulating the walls to urge the device selectively in both a forward direction (7). The stimulating means may be electrodes (5,8), and the passage can be the gut of an animal or human. The device is particularly useful as an enteroscope.

16 Claims, 3 Drawing Sheets

PASSAGE-TRAVELLING DEVICE

This application claims priority to PCf/GB00/03023, filed Aug. 3, 2000, published on Feb. 8, 2001, Publication No. WO 01/08548 A1 in the English language and which claimed priority to GB Patent Application No. 9918184.4, filed Aug. 3, 1999.

FIELD OF THE INVENTION

The present invention relates to a device, capable of propelling itself along a passage having walls containing contractile tissue.

BACKGROUND ART

Electrical stimulation has been extensively used as a method of inducing contraction of strips of muscular tissue. Further, direct smooth muscle stimulation has also been used to improve emptying of ileal and colonic pouches in animals and humans.

In addition, UK patent application 9808426.2 describes a device, such as an endoscope, having means for propelling itself along a tortuous passage by way of suction means. The means comprises a first suction means mounted on the endoscope and a second suction means mounted thereon for movement with respect to the first suction means longitudinally of the endoscope, the first and second suction means each being arranged, when actuated, to grip the tissue of a body passage in which the endoscope is disposed.

French Patent Application No. 2,237,648 discloses a device capable of being placed in the lower digestive tract as a suppository and which comprises means for agitating the walls of the tract to clear obstructions during constipation. The agitating means can operate either via electrical stimulation of the tract, by imparting mechanical vibrations to the tract, or by imparting an effect due to the liberation of a gas under pressure.

SUMMARY OF THE INVENTION

According to a first aspect of the present invention, a device is provided that is adapted to travel through a passage having walls containing contractile tissue the device comprising a body and at least one contractile tissue stimulating means for urging the device in a forward or backward direction.

According to a second aspect, the present invention provides a method of propelling a device along a passage having walls containing contractile tissue, comprising stimulating contractile tissue in the walls so as to contract the wall in contact with the device, and so urge the device in a forward or backward direction.

Preferred features of the invention will be evident from the accompanying dependent claims.

The present invention will now be further described in the following non-limiting examples as illustrated by the accompanying drawings in which:

BEST MODE

Figure 1:
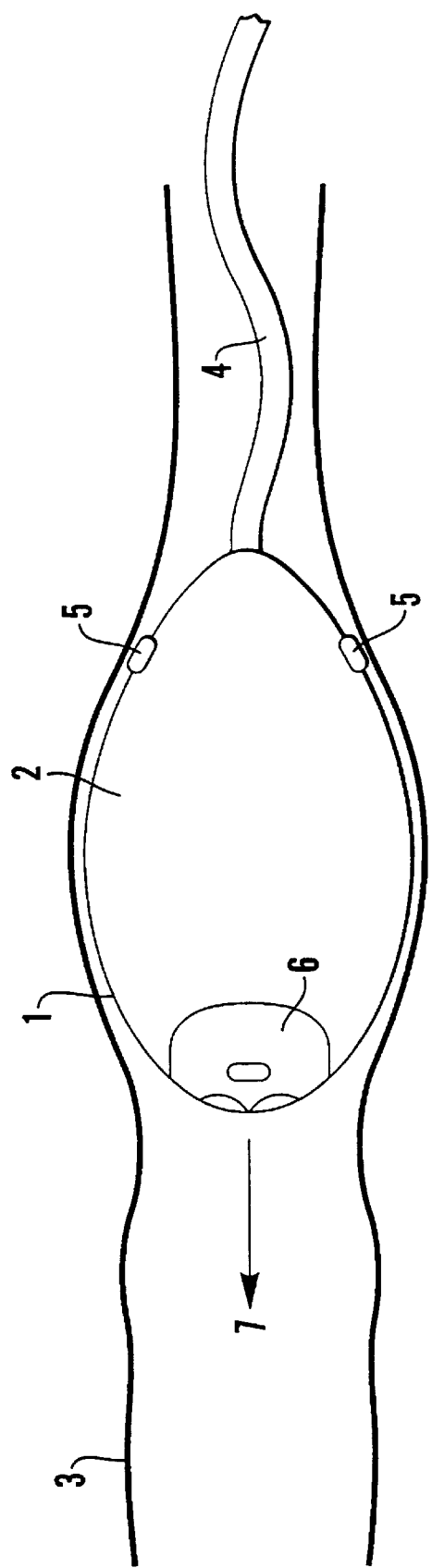
FIG. 1 represents a device, according to one embodiment of the invention, in which the stimulating means comprises a pair of electrodes located at the rear of the body of the device.

Whilst the passage through which the device (1) travels may be any passage containing contractile tissue, a particularly useful application of the device is for investigation of the gut of animals or humans. Thus, in FIG. 1 a self-propelling device (1) is shown comprising a body (2) adapted to travelling within a gut (3) of an animal or a human in a forward direction (7). On the body (2) are located stimulating means which, in FIG. 1, comprises a pair of electrodes (5). These are located toward the rear of the device on a tapered portion. In operation, the electrodes (5) electrically stimulate the smooth muscle of the gut (3) wall which contracts around only one end of the device and so squeezes the body (2) along the passage, in a similar way that natural peristalsis propels a bolus of food.

Thus, when a voltage is applied to the electrodes (5), a current flows through the wall of the gut (3) causing the smooth muscle tissue of the wall to contract around only the end of the device near the electrodes (5) and so squeeze the device (1) forwards. As the device is squeezed forwards new wall tissue is brought into contact with the electrodes (5), and so this new tissue is, in turn, electrically stimulated and so contracts to squeeze the body (2) of the device (1). The device therefore advances smoothly along the passage so long, as a stimulating voltage is applied. In this way, generalised autonomic peristalsis is not stimulated, but instead the local muscles and nerves of the gut are directly stimulated, to produce a local contraction, which is propagated by the electrodes as the device travels along the passage.

Under certain circumstances it may be preferable to view the tissues when they are inflated. Inflating the tissues may prevent a reliable electrical contact from being made but, were this to happen, the problem can be overcome by stimulating the tissues prior to inflation so as to advance the device. Once the device (1) has advanced sufficiently far along the passage, for example the colon or small bowel, the current may be switched off and the bowel inflated so that it can be viewed with a camera, the device (1) being pulled progressively back by an umbilicus (4).

Preferably, the body (2) has a substantially tapered rear portion, so that the body (2) is, for example, lozenge-shaped, hence allowing the forward movement (7) to be smooth. However, any shape of body (2) will suffice as long as the device will be urged forwards when squeezed by the gut as it contracts. Thus, the body (2) may have a shape similar to that of a rugby ball or to a cylinder with hemispherical ends. Indeed, the body (2) may also be in the form of an inflatable balloon with external electrodes (5,8) that can be inserted in an uninflated state through a small orifice into a larger part of the gut or passage, in which it is subsequently inflated ready for travel.

The umbilicus (4) may be arranged so that it can transmit information from the device (1) to a remote station, for example a screen viewed by a doctor. The nose (6) may comprise any one or more of a camera means, a light means and means for supplying air or water to inflate the passage. The device may also be used to carry objects such as feeding tubes, guide wires, physiological sensors or conventional endoscopes within the gut.

The body (2) may also comprise a rear chamber in which the umbilicus (4) can be stored and gradually paid out as the device (1) travels forward.

Generally, the electrodes (5) receive a voltage of between 2 and 10V, more preferably 3 and 5V, at a frequency of 3 Hz to 20 kHz, more preferably 10 Hz to 30 Hz.

As previously mentioned, the rear portion of the body (2) is typically tapered in shape with respect to the longitudinal axis of the body (2), and preferably at a taper angle of between 5° and 80° half angle, and preferably between 10° and 45° half angle, since such angles give a good compromise between ease of squeeze and ease of progress.

The body (2) is preferably constructed to have a length appropriate to the passageway in which it will travel. For example, in the human small bowel a length of between 1 and 5 cm, preferably between 2 and 4 cm, and a width of between 0.5 and 3 cm, preferably between 1 and 2 cm, would be appropriate.

Figure 2:
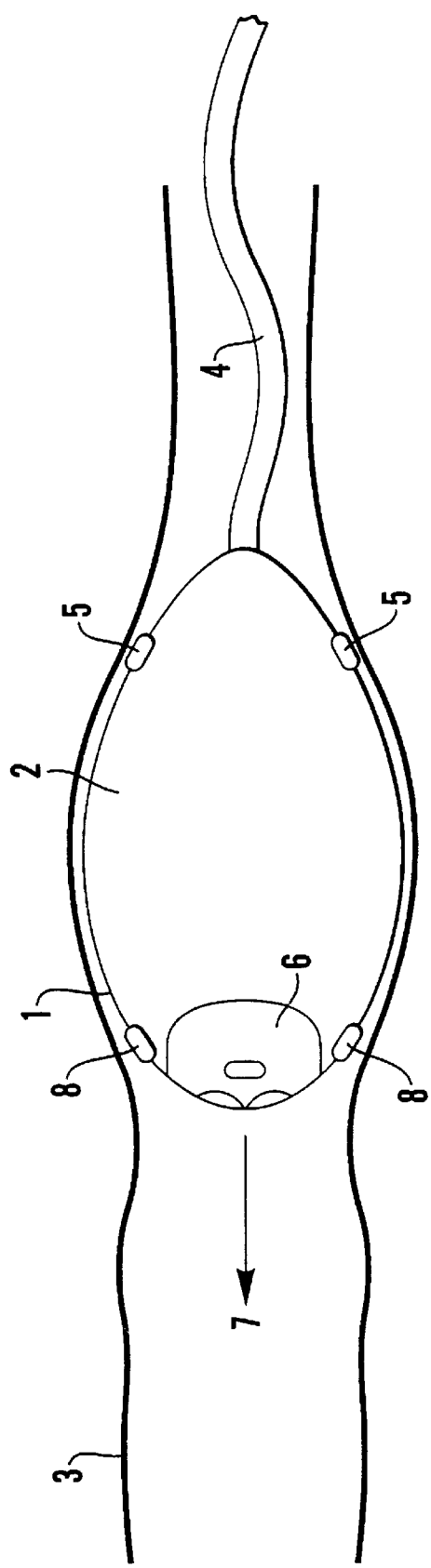
FIG. 2 illustrates a second embodiment of the present invention, in which a pair of electrodes is located both at the rear and front of the body of the device.

A second embodiment is shown in FIG. 2, in which a second pair of electrodes (8) are located on the front , or nose, end of the device's body (2). This second pair of electrodes (8) can be used to stimulate the gut (3), instead of the first pair of electrodes (5), to allow the device (1) to travel in a backward direction. Under certain circumstances, it may be desirable to lock the device (1) in one place, in which case, all electrodes (5,8) can be activated simultaneously, so that the device (1) is enclosed by contracted tissues.

Figure 3:
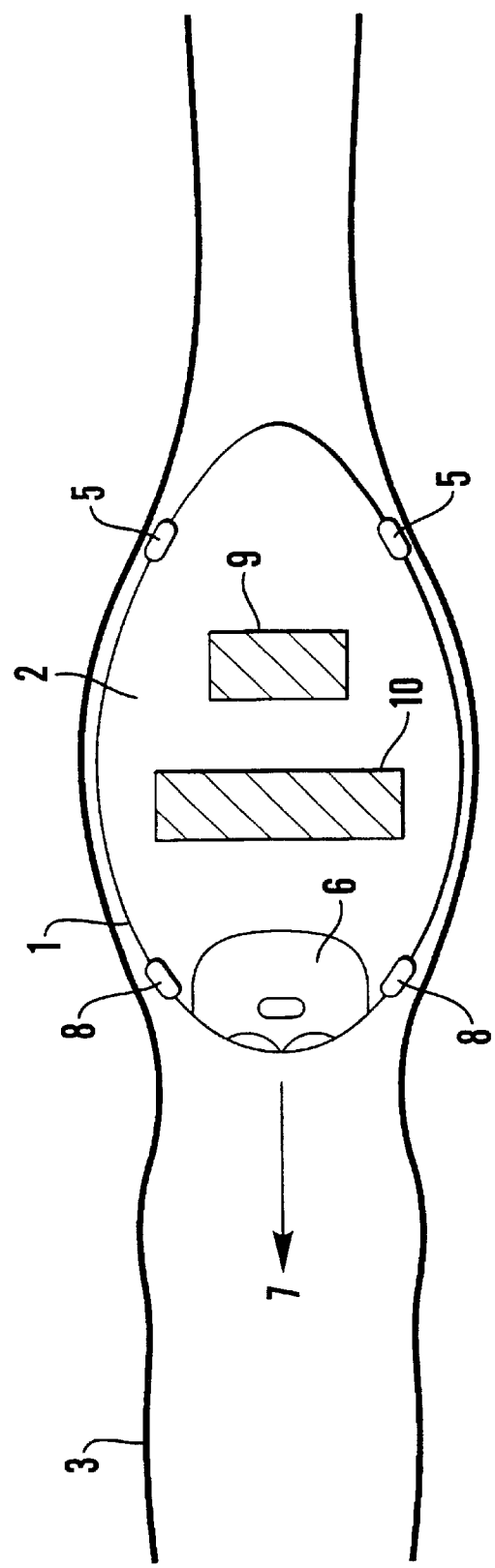
FIG. 3 illustrates a third embodiment of the present invention, which is similar to that shown in FIG. 2, but where no umbilicus is attached to the device.

In FIG. 3, a third embodiment is illustrated in which an umbilicus is absent, but instead a transmitter/receiver unit (9) is located in the body (2) allowing an operator at a remote station to communicate, and thus operate, the device (1). The absence of umbilicus necessitates the presence in the body (2) of an independent power source (10), for example a known type of battery. Electric current can thus be supplied to either pair of electrodes (5,8) according to the desired direction of travel.

A particularly attractive feature of the device described above is that it is very useful in enteroscopy, that is, the inspection of the small bowel. Enteroscopy has until now remained difficult, since the small bowel in the gastrointestinal tract is mostly inaccessible to standard endoscopy. This is because either the endoscopist must push an endoscope from the caecum or the duodenum, or he must slowly allow natural peristalsis to push an extremely flexible endoscope down through the digestive tract, so that he can observe the walls of the small bowel as the endoscope is pulled backwards.

Neither of these approaches is satisfactory, since the technical difficulties of such pushing only allow the ends of the small bowel to be investigated, whilst the long time (several hours) allowed to pass a standard endoscope is most unpleasant and impractical.

Thus, the device as described above, which is capable of carrying a small camera and a light source both rapidly and smoothly through the small bowel is of considerable benefit.

What is claimed is:

1. A device adapted to travel through a passage having walls containing local contractile tissue, the device comprising a body and at least one contractile tissue-stimulating means to urge the device selectively in both a forward and backward direction; wherein at least a rear-most portion of the body, in relation to a required direction of travel, is substantially tapered with respect to a longitudinal axis of the body, and has located thereon said at least one local contractile tissue-stimulating means.

2. A device as claimed in claim 1, wherein the contractile tissue-stimulating means is adapted to stimulate either smooth or striated muscle.

3. A device as claimed in claim 1, wherein the body is lozenge-shaped, or shaped substantially as a cylinder with hemispherical ends, or is an inflatable balloon capable of assuming a required shape upon inflation.

4. A device as claimed in claim 1, wherein the tapered body has an angle of taper of between 5° and 80° half angle.

5. A device as claimed in claim 1, wherein the body has a length of between 1 and 5 cm.

6. A device as claimed in claim 1, wherein the width of the body is between 0.5 and 3 cm.

7. A device as claimed in claim 1, further comprising an umbilicus attached to one end of the body, said umbilicus being capable of transmitting information to a remote station.

8. A device as claimed in claim 1, wherein the device is without attachment to any means passing out of the passage.

9. A device as claimed in claim 1, having at least means for transporting objects selected from the group consisting of: feeding tubes, guide wires, physiological sensors and endoscopes.

10. A method of propelling a device along a passage having walls containing contractile tissue, comprising: providing a device according to claim 1 within the passage and activating the device to stimulate local contractile tissue in the walls of the passage, so as to contract a local region of the walls in contact with one end of the device, and so urge the device selectively in both a forward and backward direction.

11. A method as claimed in claim 10, wherein the device is a discrete unit that is operated from a remote station.

12. A method as claimed in claim 10, wherein the device is an enteroscope.

13. A passage-traveling device adapted to travel through a passage having walls containing contractile tissue, the device comprising a tapered body, a plurality of electrodes disposed on the body, and means for supplying an electric current selectively to said electrodes and thereby to contractile tissue surrounding either one end of the body to urge the device selectively in both a forward and backward direction.

14. A device as claimed in claim 13, wherein said plurality of electrodes are located on either end of the body in an orientation relative to the body that is opposite to that of a required direction of travel.

15. A device as claimed in claim 13, wherein the body is associated with at least one selected from the group consisting of a camera means, a light means, means for supplying air or water to inflate the passage, means for storing energy to be supplied to the electrodes as electrical current, and means for receiving or transmitting data to a remote station.

16. A moveable, remotely-operable enteroscope comprising a discrete, tapered body; and at least one local contractile tissue-stimulating means configured to urge the enteroscope selectively in both a forward and backward direction and located, on the body, in an orientation relative to the body being opposite to a required direction of movement of the enteroscope.

* * * * *